(12) United States Patent
Nyström et al.

(10) Patent No.: US 6,524,547 B1
(45) Date of Patent: Feb. 25, 2003

(54) PROCESS FOR PRODUCING HYDROGEN PEROXIDE AND COMPOSITION THEREFOR

(75) Inventors: Mats Nyström, Ytterby (SE); Christina Järnvik, Nol (SE); Hans Thor, Bohus (SE); Seppo Saari, Kode (SE)

(73) Assignee: Akzo Nobel N.V., Arnhem (NL)

( * ) Notice: Subject to any disclaimer, the term of this patent is extended or adjusted under 35 U.S.C. 154(b) by 46 days.

(21) Appl. No.: 09/715,103

(22) Filed: Nov. 20, 2000

(30) Foreign Application Priority Data

Nov. 22, 1999 (SE) .............................. 99850175

(51) Int. Cl.$^7$ .......................... C01B 15/023; C09K 3/00
(52) U.S. Cl. ................. 423/588; 252/182.12; 423/589; 423/590
(58) Field of Search ................................ 423/588, 589, 423/590; 252/182.12

(56) References Cited

U.S. PATENT DOCUMENTS

| | | | |
|---|---|---|---|
| 3,923,967 A | * 12/1975 | Kirchner et al. | 423/588 |
| 4,258,025 A | * 3/1981 | Copelin | 423/588 |
| 4,374,820 A | 2/1983 | Guenter | 423/588 |
| 4,539,196 A | 9/1985 | Sethi | 423/588 |
| 4,552,748 A | 11/1985 | Berglin | 423/588 |
| 4,668,499 A | * 5/1987 | Rushmere | 423/588 |
| 4,800,073 A | 1/1989 | Bengtsson | 423/588 |
| 4,800,074 A | 1/1989 | Bengtsson | 423/588 |
| 4,800,075 A | * 1/1989 | Jenkins | 423/588 |
| 5,063,043 A | 11/1991 | Bengtsson | 423/588 |
| 5,147,628 A | 9/1992 | Simon | 423/588 |
| 5,342,603 A | * 8/1994 | Deremince et al. | 423/588 |
| 5,972,305 A | * 10/1999 | Park et al. | 423/588 |
| 5,985,235 A | * 11/1999 | Nyström et al. | 423/588 |
| 6,126,914 A | * 10/2000 | Ogasawara et al. | 423/588 |
| 6,153,169 A | * 11/2000 | Glenneberg et al. | 423/588 |
| 6,207,128 B1 | * 3/2001 | Sellin et al. | 423/588 |
| 6,306,359 B1 | * 10/2001 | Mathieu et al. | 423/588 |

FOREIGN PATENT DOCUMENTS

| | | |
|---|---|---|
| EP | 0453949 | 10/1991 |
| EP | 0603624 | 6/1994 |
| WO | 95/28350 | 10/1995 |
| WO | 98/28225 | 7/1998 |

OTHER PUBLICATIONS

Derwent Abstract XP–002134528 of SU 465070. (No Date).
Wayne T. Hess, "Hydrogen Peroxide," Encyclopedia of Chemical Technology Fourth Edition, vol. 13, 1995. (No Month).

* cited by examiner

Primary Examiner—Wayne A. Langel
(74) Attorney, Agent, or Firm—David J. Serbin

(57) ABSTRACT

The invention concerns a process for production of hydrogen peroxide according to the anthraquinone process comprising the steps of alternate hydrogenation and oxidation of anthraquinones and tetrahydro anthraquinones in a working solution comprising a mixture of alkyl-substituted anthraquinones and alkyl-substituted tetrahydro anthraquinones dissolved in at least one organic solvent, wherein from 10 to 55 mole % of the anthraquinones and the tetrahydro anthraquinones are substituted with one amyl group, and the molar ratio of alkyl-substituted tetrahydro anthraquinones to alkyl-substituted anthraquinones is at least 1:1. The invention also concerns a composition useful as a working solution in said process.

10 Claims, No Drawings

PROCESS FOR PRODUCING HYDROGEN PEROXIDE AND COMPOSITION THEREFOR

The present invention relates to a process for production of hydrogen peroxide according to the anthraquinone process, wherein the working solution comprises a certain mixture of anthraquinones and tetrahydro anthraquinones. The invention also concerns a solution of such anthraquinones useful as a working solution at production of hydrogen peroxide.

The most common process for production of hydrogen peroxide is the anthraquinone process. In this process substituted anthraquinones and/or tetrahydro anthraquinones dissolved in a suitable organic solvent mixture, a so called working solution, are hydrogenated to form the corresponding hydroquinones. The hydroquinones are then oxidised back to quinones with oxygen (usually air) with simultaneous formation of hydrogen peroxide, which then can be extracted with water while the quinones are returned with the working solution to the hydrogenation step.

The anthraquinone process is described extensively in the literature, for example in Kirk-Othmer, "Encyclopedia of Chemical Technology", 4$^{th}$ Ed., 1993, Vol.13, pp. 961–995.

The hydrogenation is the most critical step in the anthraquinone process. Particularly, there are problems in minimising the loss of anthraquinones and tetrahydro anthraquinones in undesired side reactions and in reaching a high concentration of hydroquinones in the working solution. It has been found that the composition of the working solution is important to overcome these problems.

WO 95/28350 discloses production of hydrogen peroxide with a working solution mainly consisting of tetrahydro ethyl- and tetrahydro amyl anthraquinones in organic solvents.

WO 98/28225 discloses production of hydrogen peroxide with a working solution consisting of ethyl- and amyl anthraquinones in organic solvents.

It has now been found possible to provide a working solution with high solubility, enabling high concentration of hydroquinones, which working solution also is highly stable against side reactions during the hydrogenation step.

Thus, the present invention concerns a process for production of hydrogen peroxide according to the anthraquinone process comprising the steps of alternate hydrogenation and oxidation of anthraquinones and tetrahydro anthraquinones in a working solution. The working solution to be hydrogenated comprises a mixture of alkyl-substituted anthraquinones and alkyl-substituted tetrahydro anthraquinones dissolved in at least one organic solvent, wherein from 10 to 55 mole %, preferably from 20 to 50 mole 35% of the anthraquinones and the tetrahydro anthraquinones are substituted with one amyl group, and the molar ratio of alkyl-substituted tetrahydro anthraquinones to alkyl-substituted anthraquinones is at least 1:1, preferably from about 2:1 to about 50:1, most preferably from about 3:1 to about 20:1. In some cases it may be appropriate to operate at a molar ratio only up to about 9:1, but it is also possible to use working solutions almost free from alkyl-substituted anthraquinones.

The amyl-substituted anthraquinones and amyl-substituted tetrahydro anthraquinones are suitably mainly made up of 2-tert-amyl- and/or 2-iso-sec-amyl-substituted anthraquinone and tetrahydro anthraquinone, preferably a mixture thereof. Preferably, also from 45 to 90 mole %, most preferably from 55 to 80 mole % of the anthraquinones and tetrahydro anthraquinones are substituted with one or several other alkyl groups, most preferably having totally from 1 to 4 carbon atoms, particularly preferably with one ethyl group. It is most preferred that the alkyl-substituted anthraquinones and tetrahydro anthraquinones are mono-substituted, preferably at the 2-position.

The use of amyl-substituted anthraquinone and amyl-substituted tetrahydro anthraquinone in the working solution means that the corresponding hydroquinones are formed in the hydrogenation step. Since the amyl-substituted hydroquinones have a significantly higher solubility than other alkyl-substituted hydroquinones, it is possible to operate with a high degree of hydrogenation without risking precipitation of hydroquinones in the working solution, even at comparatively low concentrations of amyl-substituted quinones. However, high hydrogenation degrees can only be achieved if the amount of tetrahydro anthraquinones is sufficiently high. Furthermore, losses of active quinones to degradation products increases at low concentrations of tetrahydro anthraquinones. Unwanted precipitation might also occur.

If the amount of amyl-substituted anthraquinone and amyl-substituted tetrahydro anthraquinone is too high, the density of the working solution becomes so high that it will be difficult to extract the hydrogen peroxide with water after the oxidation step. It has been found that the density is lower when the molar fraction of amyl-substituted quinones of total amounts of quinones is kept low. Preferably, the working solution has a density, measured at 20° C., from about 910 to about 980 kg/m$^3$, most preferably from about 930 to about 970 kg/m$^3$. Furthermore, amyl-substituted anthraquinone is also more complicated to produce compared to ethyl-substituted anthraquinone, which makes it a more expensive ingredient in the working solution.

The molar ratio of alkyl substituted tetrahydro anthraquinones to alkyl substituted anthraquinones in a mature working solution (a working solution used for hydrogen peroxide production during at least six months) is suitably in the same magnitude for the anthraquinones substituted with different alkyl groups. The molar ratio for each alkyl group differ preferably less than with a factor of about 2.5, most preferably less than with a factor of about 1.7.

The alkyl substituted tetrahydro anthraquinones are normally mainly made up of β-tetrahydro anthraquinones, but also some a-tetrahydro anthraquinones may occur.

Besides the direct or indirect hydrogenation to hydroquinones, many secondary reactions take place. For example, the anthrahydroquinones can react further to tetrahydro anthrahydroquinones, which in the oxidation step is converted to tetrahydro anthraquinones, the content of which thus will increase in the working solution. This means that when the process of the invention is started up, the initial working solution may contain no or only small amounts of tetrahydro anthraquinones, as they will form automatically during the course of operation. As soon as the desirable concentrations of anthraquinones and tetrahydro anthraquinones have been reached, at least a portion of the working solution is then normally treated to dehydrogenate tetrahydro anthraquinones back to anthraquinones.

Direct or indirect formation of unwanted by-products also occur, such as epoxides, octahydro anthraquinones, oxanthrones, anthrones and dianthrones. Some of these compounds, like epoxides can be converted back to anthraquinones, while others, like dianthrones, constitute an irreversible loss of active working solution. It has been found that the formation of undesired by-products can be minimised if the molar ratio of tetrahydro anthraquinones to anthraquinones is maintained within the above specified range.

It is preferred that the working solution to be hydrogenated is substantially free from unsubstituted anthraquinone and tetrahydro anthraquinone, since these compounds have been found to have poor solubility and to easily form octahydro anthrahydroquinone, which cannot readily be oxidised to form hydrogen peroxide. It is particularly preferred that the working solution to be hydrogenated substantially consists of alkyl-substituted, most preferably a mixture of amyl- and ethyl-substituted anthraquinone and tetrahydro anthraquinone in at least one organic solvent, preferably containing less than about 100 kg/m$^3$, most preferably less than about 50 kg/m$^3$ of other compounds, such as epoxides and other degradation products from the anthraquinones and/or the solvents, some of which are not even readily identifiable.

The at least one organic solvent is preferably a mixture of one or more quinone solvents and one or more, most preferably at least two hydroquinone solvents. Suitable quinone solvents may include aromatic, aliphatic or naphtenic hydrocarbons, for example benzene, alkylated or poly-alkylated benzenes such as tert-butylbenzene or trimethyl benzene, alkylated toluene or naphthalene such as tert-butyltoluene or methylnaphthalene. Suitable hydroquinone solvents may include alkyl phosphates (e.g. trioctyl phosphate), alkyl phosphonates, alkylcyclohexanol esters, N,N-dialkyl carbonamides, tetraalkyl ureas (e.g. tetrabutyl urea), N-alkyl-2-pyrrolidones and high boiling alcohols, preferably with 8-9 carbon atoms (e.g. di-isobutyl carbinol). Most preferred hydroquinone solvents are selected from alkyl phosphates, tetraalkyl ureas, cyclic urea derivatives and alkyl-substituted caprolactams. Particularly preferred hydroquinone solvents are described in the U.S. Pat. No. 4,800,073 and 4,800,074 and include alkyl-substituted caprolactams such as octyl caprolactam and cyclic urea derivatives such as N,N'-dialkyl-substituted alkylenurea.

The hydrogenation step is normally performed by contacting the working solution with hydrogen gas in the presence of a catalyst at a temperature from about 0 to about 100° C., preferably from about 40 to about 75° C., and at an absolute pressure from about 100 to about 1500 kPa, preferably from about 200 to about 600 kPa. The degree of hydrogenation (as moles hydroquinones per m$^3$ working solution) is suitably from about 350 to about 800, preferably from about 400 to about 650.

The active catalyst may, for example, be a metal selected from any of nickel, palladium, platinum, rhodium, ruthenium, gold, silver, or mixtures thereof. Preferred metals are palladium, platinum and gold, of which palladium or mixtures comprising at least 50 wt % palladium are particularly preferred. The active catalyst may be in free form, e.g. palladium black suspended in the working solution, or be deposited on a solid support such as particles used in the form of a slurry or a fixed bed. However, it is particularly preferred to use a catalyst in the form of an active metal on a monolithic support, for example, as described in U.S. Pat. No. 4,552,748 and 5,063,043. Preferred support materials are selected from silica or aluminium oxide.

Before or after the hydrogenation step, at least a portion of the working solution is preferably regenerated in one or several steps to remove water, to keep the desired ratio of tetrahydro anthraquinones to anthraquinones, to convert some of the undesired by-products from the hydrogenation or the oxidation back to active components, and to remove other undesired by-products. The regeneration may include filtration, evaporation of water, and treatment with a porous adsorbent and catalyst based on aluminium oxide.

Other steps in the overall process of producing hydrogen peroxide, such as oxidation with oxygen or air and extraction with water, may be performed in conventional manner as described in the literature.

The invention further concerns a composition useful as a working solution at production of hydrogen peroxide with the anthraquinone process. The composition comprises a mixture of alkyl substituted anthraquinones and alkyl substituted tetrahydro anthraquinones dissolved in at least one organic solvent, wherein from 10 to 55 mole %, preferably from 20 to 50 mole % of the anthraquinones and the tetrahydro anthraquinones are substituted with one amyl group, and the molar ratio of alkyl-substituted tetrahydro anthraquinones to alkyl-substituted anthraquinones is at least 1:1, preferably from about 2:1 to about 50:1, most preferably from about 3:1 to about 20:1. Regarding optional and preferred features of the composition, the above description of the process is referred to.

The invention will now further be described in connection with the following Examples, which, however, not should be interpreted as limiting the scope of the invention.

EXAMPLE 1

Three different working solutions, 1A, 1B and 1C, were prepared by solving ethyl anthraquinone and β-tetrahydro ethyl anthraquinone using the same solvent mixture (22% tetrabutyl urea, 3% trioctyl phosphate, 75% trimethyl benzene; by volume). Each solution was hydrogenated in a bench reactor equipped with a fixed bed catalyst of palladium on a silica support. 2.5 litre of working solution was kept and circulated at 30° C. in the reactor. A large excess of hydrogen was passed through the reactor at 420 kPa (abs.) until essentially all quinone was hydrogenated to hydroquinone. Results can be seen in following table:

|  | Working soltuion sample | | |
|---|---|---|---|
|  | 1A | 1B | 1C |
| Content of ethyl anthraquinone (kg/m$^3$) | 77 | 0 | 25 |
| Content of tetrahydro ethyl anthraquinone (kg/m$^3$) | 0 | 77 | 52 |
| Molar ratio (tetra): (non-tetra) | 0:1 | 1:0 | 2:1 |
| Time to precipitation (hours) | 35 | No precipitation | No precipitation |
| Hydroquinone content at precip. (moles/m$^3$) | 300 | — | — |

It is concluded that precipitation of hydrogenated quinone occurs at lower concentrations for ethyl anthraquinone compared to its tetrahydro-form and to mixtures of both.

EXAMPLE 2

Two different working solutions, 2A and 2B, were prepared by solving ethyl anthraquinone and P-tetrahydro ethyl anthraquinone using a solvent mixture of 25% tetrabutyl urea and 75% trimethyl benzene (by volume). Each solution was hydrogenated in a laboratory reactor equipped with a slurry catalyst of palladium on a silica support. 50 ml of working solution was kept and circulated at 50° C. in the reactor. Hydrogen was supplied to the reactor at 250 kPa (abs). Essentially all quinone was hydrogenated to hydroquinone in less than one hour. The hydrogenation continued for 72 hours. Composition was found by GC-analysis and results can be seen in following table:

|  | Working solution sample | |
|---|---|---|
|  | 2A | 2B |
| Start content ethyl anthraquinone (moles/m$^3$) | 254 | 0 |
| Start content β-tetrahydro ethyl anthraquinone (moles/m$^3$) | 0 | 250 |
| Content of ethyl anthraquinone and its tetrahydro-forms after 72 hr (moles/m$^3$) | 210 | 242 |

It is concluded that ethyl anthraquinone is much more susceptible to degradation during hydrogenation compared to its tetrahydro-form.

EXAMPLE 3

A sample of mature working solution, used during more than one year, was collected from an anthraquinone process, the solution thus also containing normal degradation products. Precipitation of hydroquinone was examined with this sample as such (sample 3A) and also after some addition of further quinone. Added quinone was β-tetrahydro ethyl anthraquinone (sample 3B), amyl anthraquinone (sample 3C) or β-tetrahydro amyl anthraquinone (sample 3D). By hydrogenation in a laboratory reactor with hydrogen and palladium catalyst several concentrations of hydroquinone were prepared of each sample. These samples were left at low temperature (about −10 to +15° C.) to form precipitation. Samples where precipitation barely disappeared when heated up to room temperature were taken as maximum concentration of hydroquinone. The hydroquinone concentration was determined by titration of formed hydrogen peroxide when a sample was oxidised with oxygen and extracted with water. The original sample of working solution contained mainly the β-form of tetrahydro ethyl anthraquinone but contained also a smaller fraction of the β-form. The amyl-group in added quinone is the group 2-tert-pentyl- and the group 2-sec-isopentyl-(minor fraction). Solvent in working solution was a mixture of tetrabutylurea and commercial grade of mixed aromatic hydrocarbons (mainly $C_9$ and $C_{10}$). The results are shown in the following table:

|  | Working solution sample | | | |
|---|---|---|---|---|
|  | 3A | 3B | 3C | 3D |
| Content ethyl anthraquinone (kg/m$^3$) | 66 | 65 | 65 | 64 |
| Content tetrahydro ethyl anthraquinone (kg/m$^3$) | 90 | 113 | 89 | 87 |
| Content amyl anthraquinone (kg/m$^3$) | 0 | 0 | 14 | 0 |
| Content tetrahydro amyl anthraquinone (kg/m$^3$) | 0 | 0 | 0 | 36 |
| Total hydroquinone content without precipitation (moles/m$^3$) | 393 | 398 | 390 | 462 |
| Liquid density 20° C. (kg/m$^3$) | 947 | 955 | 952 | 958 |
| Molar fraction amyl (%) | 0 | 0 | 7 | 17 |
| Molar ratio (tetra)/(non-tetra) | 1.3 | 1.7 | 1.1 | 1.8 |

It is concluded that a moderate addition of tetrahydro amyl anthraquinone will increase maximum hydroquinone content to a higher level without risk of precipitation.

EXAMPLE 4

Two samples of mature working solution, used more than 9 months, were collected from an anthraquinone processes, the solution thus also containing normal degradation products. A mixture of tetrabutyl urea (sample 4A) or octyl caprolactam (sample 4B) with a commercial grade of mixed aromatic hydrocarbons (mainly $C_9$ and $C_{10}$) were used as solvents. A minor content of trioctyl phosphate was also present in both samples. The composition of solvents were slightly modified by evaporation and addition of more of its solvent components in order to have a suitable amount of solvent containing up to about ⅓ of solvent volume as hydroquinone solvent (tetrabutyl urea or octyl caprolactam) and the rest as quinone solvent. Precipitation of hydroquinone was examined with the same method as used in example 3. The results are shown in the following table.

|  | Working solution sample | |
|---|---|---|
|  | 4A | 4B |
| Content of ethyl anthraquinone (kg/m$^3$) | 29 | 12 |
| Content of tetrahydro ethyl anthraquinone (kg/m$^3$) | 107 | 117 |
| Content of amyl anthraquinone (kg/m$^3$) | 16 | 10 |
| Content of tetrahydro amyl anthraquinone (kg/m$^3$) | 61 | 51 |
| Total hydroquinone content without precipitation (moles/m$^3$) | 645 | 620 |
| Liquid density (kg/m$^3$) | 965 | 970 |
| Molar fraction amyl (%) | 33 | 29 |
| Molar ratio (tetra)/(non-tetra) | 3.7 | 7.7 |

It is concluded that a very high hydrogenation degree can be achieved without risk for precipitation, even at relatively low concentrations of amyl anthraquinone and tetrahydro amyl anthraquinone.

What is claimed is:

1. A process for production of hydrogen peroxide according to the anthraquinone process comprising the steps of alternate hydrogenation and oxidation of anthraquinones and tetrahydro anthrequinones in a working solution, characterised in that the working solution to be hydrogenated comprises a mixture of alkyl-substituted anthraquinones and alkyl-substituted tetrahydro anthraquinones dissolved in at least one organic solvent, wherein from 10 to 55 mole % of the anthraquinones and the tetrahydro anthraquinones are substituted with one amyl group, and the molar ratio of alkyl-substituted tetrahydro anthraquinones to alkyl-substituted anthraquinones is at least 3:1.

2. A process as claimed in claim 1, wherein the molar ratio of alkyl-substituted tetrahydro anthraquinones to alkyl-substituted anthraquinones is from about 3:1 to about 50:1.

3. A process as claimed in claim 1, wherein from 45 to 90 mole % of the anthraquinones and tetrahydro anthraquinones are substituted with one ethyl group.

4. A process as claimed in claim 1, wherein from 55 to 80 mole % of the anthraquinones and tetrahydro anthraquinones are substituted with one ethyl group.

5. A process as claimed in claim 1, wherein the working solution to be hydrogenated is substantially free from unsubstituted anthraquinone and tetrahydro anthraquinone.

6. A process as claimed in claim 1, wherein the at least one organic solvent comprises one or more quinone solvents, and one or more hydroquinone solvents selected from the group consisting of alkyl phosphates, tetraalkyl ureas, cyclic urea derivatives and alkyl-substituted caprolactams.

7. A process as claimed in claim 1, wherein the hydrogenation step is performed to a degree from 350 to 800 moles hydroquinones per $m^3$ working solution.

8. A composition comprising a mixture of alkyl substituted anthraquinones and alkyl-substituted tetrahydro anthraquinones dissolved in at least one organic solvent, characterised in that from 10 to 55 mole % of the anthraquinones and the tetrahydro anthraquinones are substituted with one amyl group, and that the molar ratio of alkyl-substituted tetrahydro anthraquinones to alkyl-substituted anthraquinones is at least 3:1.

9. A composition as claimed in claim 8, wherein the composition is substantially free from unsubstituted anthraquinone and tetrahydro anthraquinone.

10. A composition as claimed in claim 8, wherein the composition comprises from 55 to 80 mole % of anthraquinones and tetrahydro anthraquinones substituted with one ethyl group.

* * * * *